US006449038B1

(12) United States Patent
Stolze (10) Patent No.: US 6,449,038 B1
(45) Date of Patent: Sep. 10, 2002

(54) DETECTING A PROCESS ENDPOINT FROM A CHANGE IN REFLECTIVITY

(75) Inventor: Jens Stolze, Dresden (DE)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/460,198

(22) Filed: Dec. 13, 1999

(51) Int. Cl.$^7$ .................................................. G01J 3/30
(52) U.S. Cl. ...................... 356/316; 356/311; 356/630; 156/345; 156/626
(58) Field of Search ................... 356/311, 38, 318, 356/630; 438/16; 216/60; 156/345, 626, 627

(56) References Cited

U.S. PATENT DOCUMENTS

| | | | |
|---|---|---|---|
| 3,612,692 A | 10/1971 | Kruppa et al. | 356/108 |
| 3,824,017 A | 7/1974 | Gatyon | 356/108 |
| 3,874,797 A | 4/1975 | Kasai | 356/118 |
| 3,985,447 A | 10/1976 | Aspnes | 356/118 |
| 4,141,780 A | 2/1979 | Kleinknecht et al. | 156/626 |
| 4,147,435 A | 4/1979 | Habegger | 356/357 |
| 4,198,261 A | 4/1980 | Busta et al. | 156/626 |
| 4,208,240 A | 6/1980 | Latos | 156/627 |
| 4,317,698 A | 3/1982 | Christol et al. | 156/626 |
| 4,328,068 A | 5/1982 | Curtis | 156/626 |
| 4,367,044 A | 1/1983 | Booth, Jr. et al. | 356/357 |
| 4,454,001 A | 6/1984 | Sternheim et al. | 156/626 |
| 4,493,745 A | * 1/1985 | Chen et al. | 156/626 |
| 4,611,919 A | 9/1986 | Brooks, Jr. et al. | 356/357 |
| 4,618,262 A | 10/1986 | Maydan et al. | 356/357 |
| 4,838,694 A | 6/1989 | Betz et al. | 356/357 |
| 4,846,928 A | 7/1989 | Dolins et al. | 156/626 |
| 4,847,792 A | 7/1989 | Barna et al. | 364/552 |
| 4,861,419 A | 8/1989 | Flinchbaugh et al. | 156/626 |
| 4,927,485 A | 5/1990 | Cheng et al. | 156/345 |

(List continued on next page.)

FOREIGN PATENT DOCUMENTS

| | | |
|---|---|---|
| EP | 0511448 | 4/1991 |
| EP | 0753912 | 1/1997 |
| WO | 9954908 | 10/1999 |

OTHER PUBLICATIONS

Klemens, et al., "High Density Plasma Gate Etching of 0.12 $\mu$m Devices with Sub 1.5 nm Gate–oxides," *Electrochemical Society Proceedings*, vol. 97–30, pp. 85–95.

Maynard, et al., "Multiwave Ellipsometry for Real–time Process Control of the Plasma Etching of Patterned Samples," *J. Va. Sci. Technol. B.*, vol. 51, No. 1, Jan./Feb. 1997, pp. 109–115.

U.S. Patent Application entitled, Inductively Coupled RF Plasma Reactor Having an Overhead Solenoidal Antenna; filed May 13, 1996; Serial No. 08/648,254; Inventors: Collins, et al.

U.S. Patent Application entitled, "Closed–Loop Dome Thermal Control Apparatus for a Semiconductor Wafer Processing System"; filed Dec. 16, 1996; Serial No. 08/767,071; Inventors: Yavelberg, et al.

PCT Search Report dated Jul. 16, 2001, European Patent Office, P.B. 5818 Patentlaan 2 NL–2280 HV Rijswijk.

*Primary Examiner*—Frank G. Font
*Assistant Examiner*—Sang H. Nguyen
(74) *Attorney, Agent, or Firm*—Ashok Janah; Joseph Bach (57) ABSTRACT

A substrate processing apparatus comprises a process chamber capable of processing a first material on the substrate. A radiation source is capable of emitting radiation that is reflected from the substrate during processing. A radiation detector is provided to detect the reflected radiation and generate a signal trace. A controller is adapted to receive the signal trace and evaluate an endpoint of processing the first material from a change in the signal trace that is distinctive of an exposure of a second material having a different reflectivity coefficient than the first material.

34 Claims, 3 Drawing Sheets

U.S. PATENT DOCUMENTS

| | | | |
|---|---|---|---|
| 4,953,982 A | 9/1990 | Ebbing et al. | 356/357 |
| 4,972,072 A | 11/1990 | Hauser et al. | 250/225 |
| 5,045,149 A * | 9/1991 | Nulty | 156/627 |
| 5,118,378 A * | 6/1992 | Moroi et al. | 356/316 |
| 5,131,752 A | 7/1992 | Yu et al. | 356/369 |
| 5,151,584 A | 9/1992 | Ebbing et al. | 250/201.4 |
| 5,362,356 A | 11/1994 | Schoenborn | 156/626 |
| 5,450,205 A | 9/1995 | Sawin et al. | 356/382 |
| 5,499,733 A | 3/1996 | Litvak | 216/38 |
| 5,503,707 A | 4/1996 | Maung et al. | 156/626.1 |
| 5,564,830 A | 10/1996 | Böbel et al. | 374/126 |
| 5,658,418 A | 8/1997 | Coronel et al. | 156/345 |
| 5,756,400 A | 5/1998 | Ye et al. | 438/710 |
| 5,810,963 A * | 9/1998 | Tomioka | 156/345 |
| 5,910,846 A * | 6/1999 | Sandhu | 356/630 |

DETECTING A PROCESS ENDPOINT FROM A CHANGE IN REFLECTIVITY

BACKGROUND

The invention relates to detection of a process endpoint during a substrate fabrication process.

In substrate fabrication processes, semiconductor, dielectric, and conductor materials, including for example materials such as polysilicon, silicon dioxide, aluminum and tungsten silicide, are formed on a substrate by chemical vapor deposition (CVD), physical vapor deposition, oxidation and nitridation processes. For example, in CVD processes, a reactive gas may be used to deposit material on the substrate, and in PVD processes, a target is sputtered to deposit material on the substrate. In oxidation and nitridation processes, an oxide or nitride material, such as silicon dioxide or silicon nitride, respectively, is formed on the substrate by exposing the substrate to a suitable gaseous environment. In subsequent etching processes, a mask of photoresist or hard mask material is formed on the substrate by conventional lithographic methods, and the exposed portions of the substrate are etched by a gas to form patterns of gates, vias, contact holes or interconnect lines. Especially in the etching processes, it is often desirable to change or stop processing of the substrate at a predetermined stage of the process. For example, when etching polysilicon material deposited over features of a silicon nitride mask layer, it is desirable to stop etching when the silicon nitride mask layer is reached and thereafter partially etching polysilicon plugs exposed between the silicon nitride layer. As another example, in the etching of gate structures, it is desirable to stop etching of overlying polysilicon as soon as the underlying gate oxide is reached, especially when the gate oxide is a thin layer.

In plasma emission analysis, an emission spectrum of a plasma in the chamber is analyzed to monitor the etching process as for example taught in U.S. Pat. Nos. 4,328,068 and 5,362,256, both of which are incorporated herein by reference. The plasma emission spectrum depends upon the energized plasma species which are dependent upon the composition of the material being etched. When the composition of the material changes, for example, when a layer has completed etching and an underlayer is exposed, the spectral change that occurs in the plasma is used to detect completion of etching of the overlying material. In general, plasma emission methods monitor a predetermined wavelength in the plasma spectral emission and correlate variations in intensity of the wavelength with an endpoint of the process. However, such spectral changes occur only after a large portion of a new material is exposed on the substrate. Thus plasma emission analysis tends to provide information relating to an average state of processing across the surface of the substrate. This may lead to some regions being over-etched while others are under-etched.

Ellipsometry and interferometry are also be used to monitor the etching process. In ellipsometry, a polarized light beam reflected off the substrate being etched is analyzed to determine a phase shift and change in magnitude, as for example disclosed in U.S. Pat. Nos. 3,874,797 and 3,824,017, both of which are incorporated herein by reference. In interferometry, a light beam reflected off the substrate is monitored and an etching depth is determined by counting maxima and minima in the amplitude of the reflected beam or from cessation of the signal, as for example disclosed in U.S. Pat. No. 4,618,262 to Maydan et al, which is also incorporated herein by reference. The constructive and destructive interference occurs because the light beam is partially reflected off the substrate surface and partially reflected off underlying interfaces. If the original thickness of the layer is known, a remaining thickness may be estimated by counting the maxima/minima peaks during etching. While these methods may be used to estimate the amount of remaining material, it is difficult to precisely determine the end of etching of the material, especially when the original thickness of the material varies slightly from one substrate to another or across the surface of the substrate itself. Also, the area on the substrate from which initial thickness measurements are obtained is often not the same area as that from which the reflected beam is monitored, which may give rises to erroneous measurements.

Thus, it is desirable to precisely detect an endpoint of processing of a material on a substrate, especially to detect an endpoint of etching a layer on a substrate to expose an underlayer. It is further desirable for the endpoint detection method and apparatus to be relatively insensitive to changes in thickness of the layer across the substrate or from one substrate to another.

SUMMARY

Embodiments of the present invention satisfy these needs, in principle, by detecting an endpoint of a process performed on a substrate with accuracy and repeatability. In one aspect, the present invention comprises a substrate processing apparatus comprising a process chamber capable of processing a first material on the substrate. A radiation source is capable of emitting radiation that is reflected from the substrate during processing. A radiation detector is provided to detect the reflected radiation and generate a signal trace. A controller is adapted to receive the signal trace and evaluate an endpoint of processing the first material from a change in the signal trace that is distinctive of an exposure of a second material having a different reflectivity coefficient than the first material.

In one version, the apparatus comprises a computer having a memory capable of operating a computer-readable program embodied on a computer-readable medium, the computer readable program including program code to receive the signal trace and detect the change in the signal trace.

In another aspect, the present invention relates to a method of processing a substrate, in which, the substrate is placed in a process zone, and process conditions are set in the process zone to process a first material on the substrate. Radiation reflected from the substrate during processing is detected and an endpoint of processing the first material is determined from a change in intensity of reflected radiation that is distinctive of exposure of a second material having a different reflectivity coefficient than the first material.

In another aspect, the present invention relates to a substrate processing apparatus comprising a process chamber capable of sustaining a plasma to process a first material on the substrate. A first radiation detector detects a radiation emission from the plasma and generates a first signal, and a second radiation detector detects a reflected radiation from the substrate and generates a second signal. A controller is adapted to receive the first and second signals and determine an endpoint of processing of the first material on the substrate.

In one version, the apparatus comprises a computer having a memory capable of operating a computer-readable program embodied on a computer-readable medium, the computer readable program including program code to receive the first and second signals and determine an endpoint of processing the first material on the substrate.

In another aspect, the present invention relates to a method of processing a substrate, in which, the substrate is placed in a process zone, and a plasma of process gas is formed in the process zone to process a first material on the substrate. Radiation emitted by the plasma and radiation reflected from the substrate are detected. An endpoint of processing the first material is determined from a change in the radiation emitted by the plasma and a change in the radiation reflected from the substrate.

DRAWINGS

These and other features, aspects, and advantages of the present invention will be better understood from the following drawings, description and appended claims, which illustrate exemplary features of the invention, however, it is to be understood that each of the features can be used in the invention in general, not merely in the context of a particular drawing, and the invention includes any combination of these features.

DESCRIPTION

The present invention is useful for monitoring a process conducted on a substrate 20, and especially useful for detecting an endpoint of processing of a material on the substrate 20. As illustrated in the example shown in FIGS. 1a and 1b, the process may be used to detect completion of processing of a first material 22 and exposure of an underlying second material 24. Generally, the substrate 20 comprises a plurality of materials 22, 24 formed on a wafer 26 of silicon, compound semiconductor or dielectric. During processing of the materials 22, 24 it may be desirable to stop processing upon reaching an interface 23 between the first material 22 and the second material 24 or after completion of processing one or both of the first or second materials 22, 24. For example, in a typical etching process, it may be desirable to stop etching after etching through the first material 22 or after etching through only a small portion of the underlying second material 24.

The process may be illustrated referring to a typical etching process, in which a substrate 20 having the layers 22, 24 is placed in a process zone and process conditions are set for processing the substrate 20 in an energized process gas or plasma, for example to etch the first material 22. During etching, the plasma emits radiation that is characteristic of the first material 22 being etched, generally, because the plasma contains volatilized gaseous species or compounds of the first material 22 that emit a characteristic spectrum or wavelength of radiation when energized. The intensity fluctuations of radiation having the preselected wavelength is monitored to determine the rate of progress of etching of the first material 22. Because the radiation intensity (at the preselected wavelength) is dependent upon the amount of material in the plasma that emits radiation in the particular characteristic or signature wavelength, it is also dependent upon the exposed area of the first material 22 and is indicative of the average etching state of the exposed surface of the substrate 20. Thus, plasma emission analysis allows monitoring of a non-localized or global etching behavior across a substantially the entire substrate 20.

Figure 2:
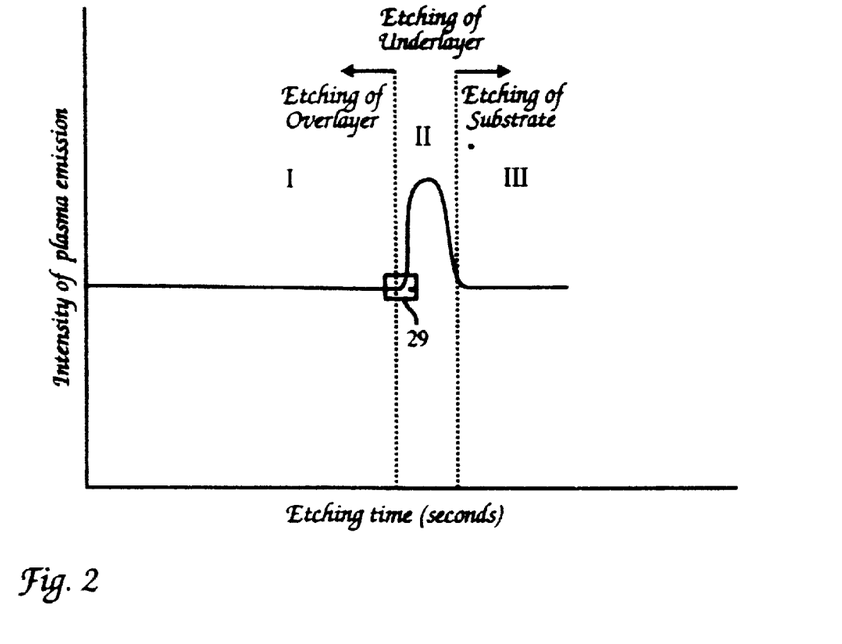
FIG. 2 is a signal trace of the intensity of radiation having a wavelength of 704 nm emitted by the plasma during processing of the substrate.

As an example, FIG. 2 shows a trace of the intensity of the plasma emission radiation at a wavelength of 704 nm. The trace represents the radiation intensity observed during etching of a polysilicon layer (first material 22) overlying a silicon nitride layer (second material 24). After etching, plugs of polysilicon material 27 are left behind between expanses of the silicon nitride layer 24 and/or exposed silicon 26. The etching process is performed to clean up polysilicon that is incidentally deposited on the silicon nitride 24 while filing the plugs 27. Referring to FIG. 2, in the first stage 1, during etching of the overlying polysilicon 22, the emission intensity remains relatively flat and at a constant level. The second etching stage 11, corresponding to the completion of etching of the underlying silicon nitride 24, shows a peak in the intensity of radiation emissions having the preselected wavelength. When all the underlayer 24 is etched away, the radiation intensity drops down to another level in stage III, in which the substrate 26 is being etched. The plasma emission curve allows the operator to select a point 29 at which the slope of the radiation emission curve begins to rise (which indicates commencement of etching of the underlayer 24) to determine the endpoint of etching of the overlayer 22.

Figure 1A:
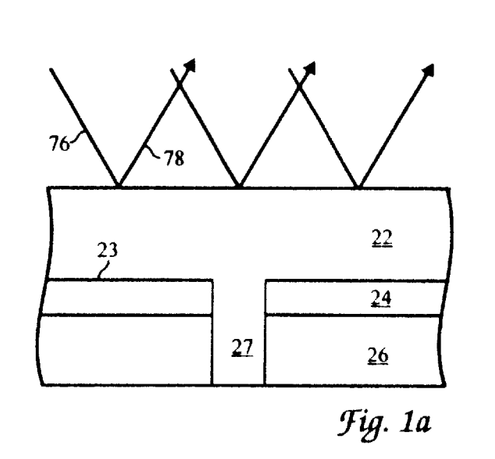
FIG. 1a is a schematic sectional view of a substrate showing the partial reflection and partial absorption of incident radiation during processing of a first material on the substrate.
Figure 1B:
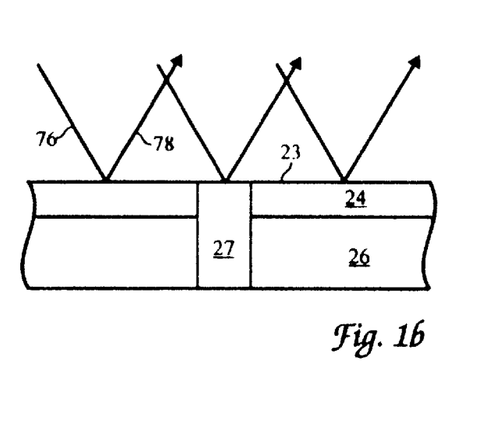
FIG. 1b shows the substrate of FIG. 1a, after completion of etching of the first material showing radiation being reflected from the surface of an underlying second material.

In addition to the plasma emission analysis, the intensity of radiation reflected from the surface of the substrate 20 is also monitored. In this method, radiation incident on the substrate 20 is partially absorbed and partially reflected from the materials 22, 24 that are being processed on the substrate 20. Generally, referring to FIG. 1a, when an optically absorbing material 22 (medium 1) lies on another material 24 (medium 2), the absorption and reflectivity of radiation may be approximately described by a summation equation. The radiation in the process environment (medium 0) that is incident on the material 22 has a first surface reflection determined by the complex Fresnel coefficient $r_1=(n_0-n_1)/(n_0+n_1)$ where $n_0$ and $n_1$ are the complex refractive indices of media 0 and 1. The complex refractive index n is defined as $n=n-ik$ where n and k are the real and imaginary parts, being the refractive index and extinction coefficient, respectively. As shown in FIG. 1a, when the material 22 has a certain thickness, a portion of the incident radiation 76 is reflected as the component 78 and another portion is transmitted into the material 22 according to the complex Fresnel transmission coefficient $t_1=2n_0/(n_0+n_1)$. The transmitted radiation is absorbed in the material 22 as a function of the depth d by the factor $\exp(-4\pi k_1 d/\lambda)$ where $\lambda$ is the wavelength of the incident radiation. If the incident radiation has not been fully absorbed before reaching the interface 23 at the rear of the material 22 some of the radiation is reflected back according to the equation, $r_2=(n_1-n_2)/(n_1+n_2)$, where $n_2$ is the complex refractive index for material 22. The part of the reflection which remains after absorption during the round trip is transmitted back into process environment—where it combines with the original reflected radiation but with a phase change $\delta=2\pi n_1 d_1/\lambda$ which depends upon the round trip distance covered in the depth d. The net reflected amplitude is approximately, $r_{net} \approx r_1+t_1t_1' r_2 \exp(+2i\delta) \exp(-4\pi k_1 d/\lambda)$, where multiple reflections have been neglected. Explicit formulations may be found in references such as M. Born and E. Wolf, *Principles of Optics*, Pergamon Press (1965), which is incorporated herein by reference. When d and k, are large enough, absorption dominates and the second term is essentially zero, producing a constant net reflection as a function of thickness. However, when the material 22 is completely etched, for example, as shown in FIG. 1b, there is a net reflection from the surface of the underlying silicon nitride material 24 and the remaining surface of the polysilicon plug 27 that contributes to the total amplitude or intensity of the reflected radiation. In between, the amplitude of the reflected radiation may vary from the changing phase and magnitude of the second term through the interface between the two materials, and as the thickness d is changed. Depending on the magnitude of $k_1$, the variation in total reflected intensity with $d_1$ can appear periodic, with an increasing amplitude as $d_1$ tends to zero. After the first material has been etched and entirely removed, the incident radiation 76 is partially reflected from the surface of the polysilicon plugs 27 and partially reflected from the surface of the silicon nitride material 24, and additional multiple internal reflections may occur from underlying layers and interfaces (not shown). The sum of the reflected components results in another observed amplitude of reflected radiation that may be different from the previously observed periodic variation in intensity.

Figure 3:
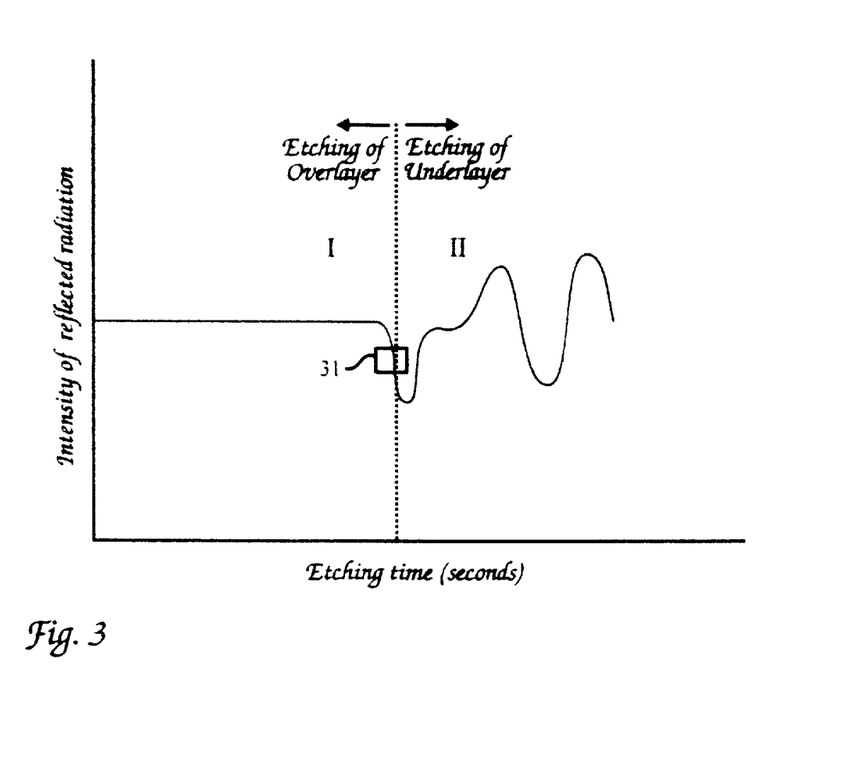
FIG. 3 is a signal trace of the intensity of radiation having a wavelength of 253.7 nm reflected from the substrate during processing of the substrate.

FIG. 3 shows the amplitude trace of reflected radiation obtained during etching of the same type of substrate 20 as that described above, namely one with polysilicon 22 overlying silicon nitride 24. In this example, a wavelength of 253.7 nm was chosen to irradiate the substrate 20 because it is one of the peak amplitudes of radiation of-an emission spectra from a mercury discharge lamp. In the first stage 1, during etching of the overlying polysilicon layer 22, the intensity of the reflected radiation remains relatively flat. The second etching stage 11, corresponding to the etching of the underlying silicon nitride layer 24, shows a minima peak having a downward slope that corresponds to the etching away or clear-off of residual regions of polysilicon left in the field of view of the sensor. After the silicon nitride layer is exposed, the polysilicon plug 27 is etched at a faster rate than the surrounding silicon nitride 24. As a result, there is a difference in path length for the radiation reflected from the surface of the polysilicon plug 27 relative to the radiation reflected from the surface of the silicon nitride 24, which gives rise to periodic variations that correspond to maxima and minima interference peaks. This type of curve may be used to detect a precise endpoint of completion of etching of the polysilicon overlayer 22 and onset of etching of the underlayer 24 (at the point 31 where the curve has sloped downward for a short time period) to ensure complete removal of residual polysilicon. This is advantageous because it allows selection of a different gas chemistry when the polysilicon 22 is substantially entirely etched away, to allow etching away of a portion of the plug 27 with a different gas chemistry that, for example, may have a higher etching selectivity to etching silicon nitride relative to polysilicon.

Thus, the intensity of the reflected radiation may be monitored and evaluated to determine a change in amplitude of reflected radiation that occurs during processing of the first and second materials 22, 24 from the difference in reflectivity between one or more of the first material 22, second material 24, or their interface 23. For example, when radiation passes through the first and second materials 22, 24, the second material 24 may have a different reflectivity coefficient or function than the first material 22 which would cause a smaller or larger percentage of radiation to be reflected from the surface of the second material 24 than that reflected from the first material 22. In addition, the interface 23 may also have a different reflectivity coefficient or function than the materials 22, 24 which would affect the amount of radiation reflected from the interface 23. The empirically observed change in the amplitude trace is precisely correlated to the change in reflectivity that occurs after etching through one layer 22 and at the interface 23 of a second layer 24. This is typically a precise and sharply defined change that it is believed results substantially only from the change in reflectivity coefficient of the two materials and may be used to pinpoint the endpoint of the etching of the first layer 22 and reaching the environment of etching the second layer 24 accurately and decisively.

Additional precision may be obtained by focusing the incident radiation onto a precise area or region of the substrate 20 containing a known thickness of polysilicon material 22. The localized reading of the change in reflectivity at the completion of etching of the localized region provides especially useful information when evaluated together with the average or global reading obtained across the surface of the substrate 20 by plasma emission analysis. The two readings are evaluated to determine both the average etching rate and local etching rate, and are concurrently detected to chose an endpoint which is more accurate than a single reading from any one of the methods. In addition, the two readings may be used to determine if there is any deviation in etching rates or in the original thickness of the polysilicon layer from substrate to substrate or across a batch of substrates. A particular set of measurements may be empirically determined as a reference point for a batch of substrates. When future measurements on other batches deviate from these reference values, it could mean that the thickness of one of the materials 22, 24 has changed and the endpoint time should be adjusted in accordance with the deviation.

While the relationship between the amplitude change of reflected radiation in the etching of a first material 22 and exposure of a second material 24 may be established based on empirical data, it may also be estimated by a radiation absorption model with the appropriate parameters and assumptions, and knowing values for other parameters of the first and second materials 22, 24, e.g., its composition, refractive index, extinction coefficient, thickness, and other radiation absorption and reflection constants; an etch rate and etching selectivity of the process; and an area of overlying mask material. A trace of the estimated amplitude change may be mathematically calculated for given thicknesses of the first and second materials and be stored as a reference trace or as a table of values. The reference trace or values in the table may be compared against an empirically determined signal trace to determine the stage or endpoint of the etching process.

Figure 4:
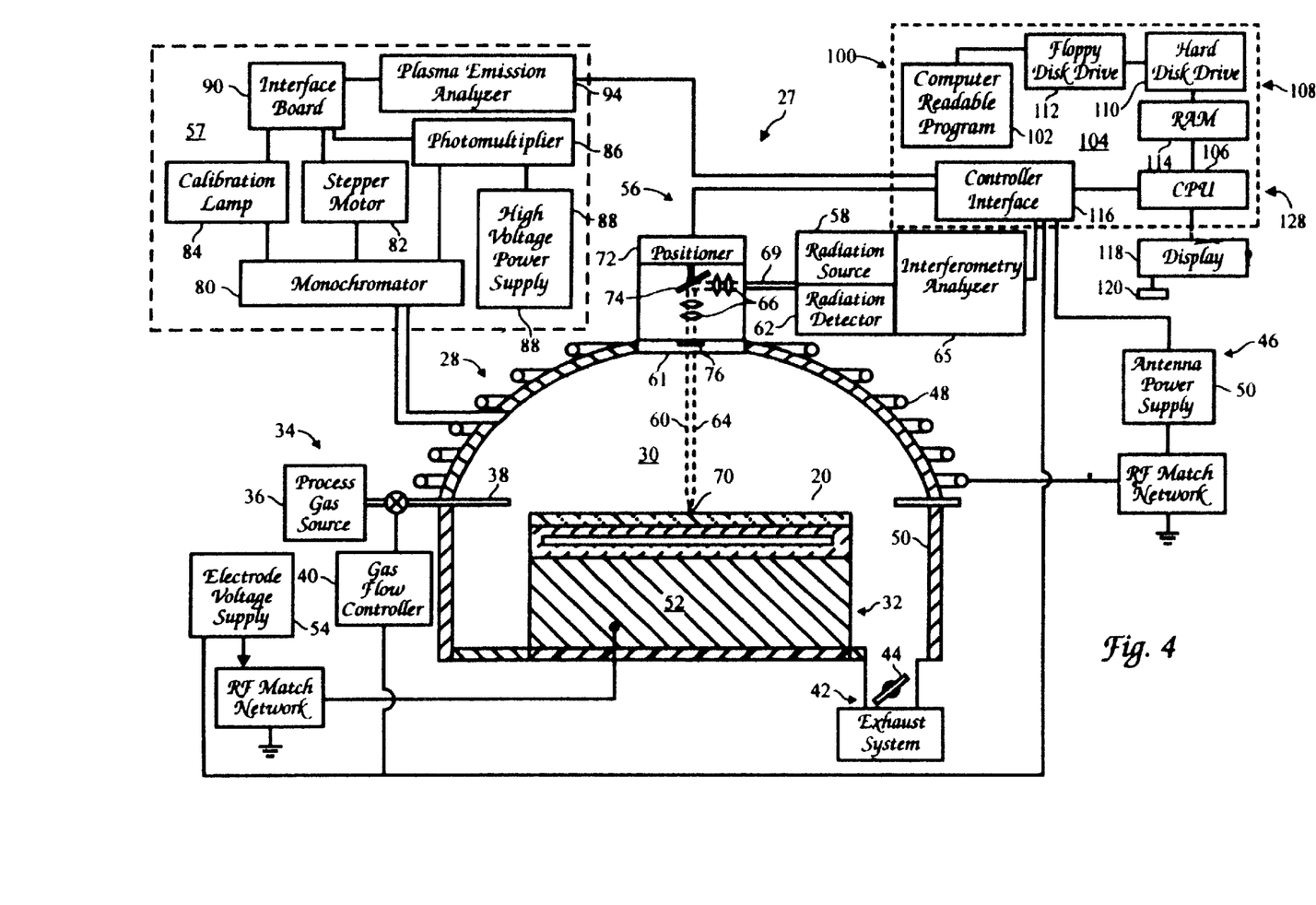
FIG. 4 is a schematic sectional side view of a chamber and process monitoring system according to the present invention.

The examples provided herein, may be used, for example, in the etching of a substrate 20 in the apparatus 27 that is schematically illustrated in FIG. 4. Generally, the apparatus 27 comprises a chamber 28 having a process zone 30 for processing the substrate 20 and a support 32 to receive the substrate 20 in the process zone 30. The process gases are introduced into the chamber 28 through a gas supply 34 comprising a gas source 36, gas outlets 38 located around the periphery of the substrate 20 (as shown) or in a showerhead mounted on the ceiling of the chamber (not shown), and a gas flow controller 40 for controlling the flow rate of the process gas. Spent process gas and etchant byproducts are exhausted from the chamber 28 through an exhaust 42 comprising roughing and turbomolecular pumps (not shown) and a throttle valve 44 is used to control the pressure of process gas in the chamber 28.

An energized gas or plasma is generated from the process gas by a gas energizer 46 that couples RF or microwave energy to the process gas in the process zone 30 of the chamber 28, such as for example, an inductor antenna 48 comprising one or more coils powered by an antenna power supply 50 to inductively couple RF energy to the chamber 28. In addition, a first process electrode 50 such as an electrically grounded sidewall of the chamber 28 and a second electrode 52 such as an electrically conductor below the substrate 20 may be used to further energize the gas in the chamber 28. The first and second electrodes 50, 52 are electrically biased relative to one another by an RF voltage provided by an electrode voltage supply 54. The frequency of the RF voltage applied to the inductor antenna 48 and the electrodes 50, 52 is typically from about 50 KHz to about 60 MHz.

The chamber 28 further comprises a process monitoring system 56 to monitor the process being performed on the substrate 20. The interferometric analysis system 56 comprises both an interferometric analysis system 56 and a plasma emission analysis system 57. The radiation source 58 may provide radiation such as ultraviolet (UV), visible or infrared radiation; or may provide other types of radiation such as X-rays. The radiation source 58 may comprise, for example, an emission from a plasma generated inside the chamber 28, the plasma emission being generally multispectral, i.e., providing radiation having multiple wavelengths extending across a spectrum, such as polychromatic radiation. The radiation source 58 may also be positioned outside the chamber 28 so that a radiation beam 60 may be transmitted from the source 58 through a window 61 and into the chamber 28. The radiation source 58 may also provide substantially monochromatic radiation having predominant wavelengths, or a single wavelength such as monochromatic light for example, a He—Ne or Nd-YAG laser. Alternatively, the radiation source 58 may provide radiation having multiple wavelengths, such as polychromatic light, which may be selectively filtered to a single wavelength. Suitable radiation sources 58 for providing polychromatic light include Hg discharge lamps that generate a polychromatic light spectrum having wavelengths in a range of from about 180 to about 600 nanometers; arc lamps such as xenon or Hg—Xe lamps and tungstenhalogen lamps; and light emitting diodes (LED).

In one version, the radiation source 58 provides a source of nonpolarized light, such as ultraviolet, infrared or visible light directly above the substrate 20. One reason is that variations in the intensity of polarized radiation reflected from the substrate 20 can be masked by changing absorption characteristics of the energized gas or plasma. In addition, the state of polarization of the radiation also influences its absorption in materials having oriented crystalline structures, such as crystals having other than cubic symmetry. Also, the polarization state of the radiation can change when it passes through a thin residue film that deposits on the window 61 of the chamber 28 during the process, and the polarization state also changes as the thickness of the residue film increases, which gives rise to erroneous measurements. Thus, for certain processes, depending on the process gas composition and the location of the source of radiation, it may be preferred to use a radiation source 58 providing unpolarized radiation. A normal incidence of the radiation onto the substrate 20 can reduce such effects. Normal incidence also provides a more accurate endpoint reading for a substrate 20 having tall and narrowly spaced features over the layers 22, 24, because the normally incident radiation is not blocked from reaching the layers 22, 24 by the height of the narrow features. The radiation source is mounted above the substrate to direct a radiation beam at an incident angle of about 80 to 90 degrees onto the substrate. However, the normal incidence is not necessary for detection of the reflected radiation and other angles of incidence may be employed.

The interferometric system 56 further comprises a radiation detector 62 for detecting radiation 64 reflected by the substrate 20. The radiation detector 62 comprises a radiation sensor, such as a photovoltaic cell, photodiode, photomultiplier, or phototransistor, which provides an electrical output signal in response to a measured intensity of a reflected beam of radiation 64 (or an emission spectra from the plasma). The signal may comprise a change in the level of a current passing through an electrical component or a change in a voltage applied across an electrical component. A suitable system for coupling the radiation detector 62 to the chamber 28 comprises a fiberoptic cable 69 leading to the sensor of the radiation detector 62. The process endpoint data processed by the detectors 62 is transmitted to an interferometric analyzer 65 appropriate through interface boards to allow analysis of the data.

Optionally, a lens assembly 66 may be used to focus a radiation beam 60 emitted by the radiation source 58 onto the substrate 20, or to focus a radiation beam 64 reflected back from the substrate 20 onto the sensor of the radiation detector 62. For example, for a radiation source 58 comprising a Hg-discharge lamp located outside the chamber 28, a plurality of lenses 66 may be used to focus a radiation beam 60 from the lamp through the window 61 and onto a beam spot 70 on the substrate 20. The area of the beam spot 70 should be sufficiently large to provide an accurate measurement of the surface topography of the substrate 20. The lenses 66 may also be used to focus reflected radiation 64 back onto the sensor of the radiation detector 62 in the reverse direction which is especially useful when the radiation source 58 is a plasma emission.

Optionally, a positioner 72 may be used to scan the incident radiation 60 across the substrate surface to locate a suitable portion of the substrate 20 on which to "park" the beam spot 70. The positioner 72 may comprise one or more primary mirrors 74 that can rotate at small angles to deflect radiation from the radiation source 58 onto different positions of the substrate surface (as shown). Alternatively, the mirrors 74 can also direct radiation emitted from a plasma emission and at least partially reflected off the substrate 20 back onto the radiation detector 62. Additional secondary mirrors (not shown) may be used to intercept and focus reflected radiation back on the radiation detector 62. The positioner 72 can also be used to scan radiation in a raster pattern across the substrate 20. In this version, the positioner 72 further comprises a movable stage (not shown) upon which the radiation source 58, lens assembly 66, and radiation detector 62 are mounted. The movable stage may be moved through set intervals by a drive mechanism, such as a stepper motor, that scans or otherwise moves the beam spot 70 across the substrate 20.

Radiation having a plurality of wavelengths, such as polychromatic light from a lamp or a plasma emission spectra, can be suitable filtered by placing a filter 76 in the path of the incident or reflected radiation 60, 64. The filter 76 is typically located in the lens assembly 66 but can also be located at other positions in the chamber 28, for example, in the chamber window 61, in front of the radiation detector 62, or in front of the radiation source 58. A suitable filter 76 comprises thin films on a transparent support that selectively transmit radiation having the desired wavelength, a filtering lens, a diffraction grating having a diffraction spacing that scatters radiation having undesirable wavelengths, attenuation of radiation through a long pathlength in a partially absorbing material, or selective electronic filtering of the signal from the radiation detector 62 to read only the portion of the signal corresponding to radiation having the desired wavelength.

The plasma emission analysis system 57 comprises a monochromator 80, a stepper motor 82 that controls the wavelength selection for the monochromator 80, and a calibration lamp 84 that calibrates the monochromator 80. The monochromator 80 selects monochromatic wavelengths and the radiation signal is amplified by a photomultiplier 86 powered by a high voltage power source 88. The output of the photomultiplier 86 is coupled to the monochromator interface board 90. The stepper motor 82 allows selection of a particular wavelength for monitoring the process being conducted on the substrate 20 controlling the position of an interference grid within the monochromator 80 to select a wavelength. The interface board 90 is also coupled to the calibration lamp 84 to calibrate the monochromator 80 at a particular wavelength. Alternatively, the monochromator-based system can be replaced by a bandpass photon detector system, such as the system disclosed in U.S. patent application Ser. No. 08/800,003, filed Feb. 13, 1997, and incorporated herein by reference. The radiation data is supplied to an analyzer 94 through an electronic interface board 189. The analyzer 94 may be a spectrometer that separates the components of the radiation emanating from the chamber 28, according to their frequency or wavelength. Such analyzers include, but are not limited to, grating spectrometers, prism spectrometers, and band pass screen arrays, for example, a HOT pack manufactured by Applied Materials, Inc. of Santa Clara, Calif. Alternatively, the analyzer may be a component of the detector, controller, or other such devices.

The chamber and endpoint detection system 56 is operated by a controller 100 that executes a computer-readable process control program 102 on a computer system 104 comprising a central processor unit (CPU) 106, such as for example a 68040 microprocessor, commercially available from Synergy Microsystems, Calif., or a Pentium Processor commercially available from Intel Corporation, Santa Clara, Calif., that is coupled to a memory 108 and peripheral computer components. The memory 108 comprises a computer-readable medium having the computer-readable program 102 embodied therein. Preferably, the memory 108 includes a hard disk drive 110, a floppy disk drive 112, and random access memory 114. The computer system 104 further comprises a plurality of interface cards including, for example, analog and digital input and output boards, interface boards, and motor controller boards. The interface between an operator and the computer 104 can be, for example, via a display 118 and a light pen 120. The light pen 120 detects light emitted by the monitor 118 with a light sensor in the tip of the light pen 120. To select a particular screen or function, the operator touches a designated area of a screen on the display 118 and pushes the button on the light pen 120. Typically, the area touched changes color, or a new menu is displayed, confirming communication between the user and the controller 110. The computer 104 communicates with the chamber 28 and process monitoring systems 56, 57 via a controller interface 116 which has a plurality of interface boards and other cards.

The computer-readable program 102 stored on the memory 108 or other computer program product inserted in the disk drive 112, may also be used to operate the controller 100. The computer program 102 generally comprises software to operate the chamber 28 and its components to monitor the processes, to activate safety systems, and other control software. The computer program 102 may be written in any conventional programming language, such as for example, assembly language, $C^{++}$, Pascal, or Fortran. Suitable program code is entered into a single file, or multiple files, using a conventional text editor and stored or embodied in the memory 108 of the computer system 104. If the entered code text is in a high level language, the code is compiled, and the resultant compiler code is then linked with an object code of precompiled library routines. To execute the linked, compiled object code, the user invokes the object code, causing the CPU 106 to read and execute the code to perform the tasks identified in the program.

Figure 5:
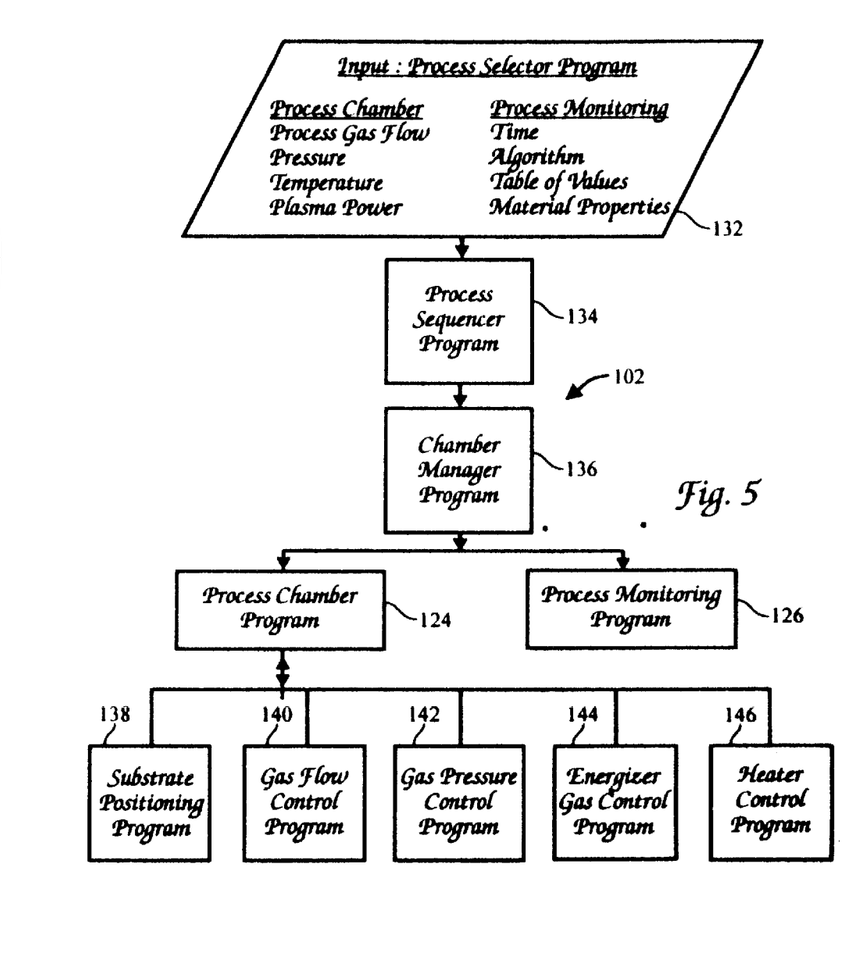
FIG. 5 is an block diagram of the structure of an illustrative computer program suitable for operating the chamber and monitoring the process.

FIG. 5 is an illustrative block diagram of a hierarchical control structure of an exemplary embodiment of a computer program 102 according to the present invention. Using a light pen interface, a user enters a process set and chamber number into a process selector program 132 in response to menus or screens displayed on the CRT terminal. The process sets are predetermined groups of process conditions necessary to carry out a process in a chamber 28 including without limitations, gas composition, gas flow rates, temperature, pressure, gas energizer settings such as RF or microwave power levels, cooling gas pressure, and wall temperature. In addition, parameters needed to operate the process monitoring systems 56, 57 are also inputted by a user into the process selector program. These parameters include known properties of the materials being processed, especially radiation absorption and reflection properties, such as reflectance and extinction coefficients; process monitoring algorithms that are modeled from empirically determined data; tables of empirically determined or calculated values that may be used to monitor the process; and properties of the materials being processed on the substrate.

The process sequencer program 134 comprises program code to accept a process chamber 28 and set of process parameters from the process selector program 132 and to control its operation. The sequencer program 134 initiates execution of the process set by passing the particular process parameters to a chamber manager program 136 that controls multiple processing tasks in the process chamber 28. The process chamber program 124 includes program code to set the timing, gas composition, gas flow rates, chamber pressure, chamber temperature, RF power levels, support position, heater temperature, and other parameters of a particular chamber 28. Typically, the process chamber program 124 includes a substrate positioning program 138, a gas flow control program 140, a gas pressure control program 142, and a gas energizer control program 144. Typically, the substrate positioning program 138 comprises program code for controlling chamber components that are used to load the substrate 20 onto the support 32 and optionally, to lift the substrate 20 to a desired height in the chamber 28 to control the spacing between the substrate 20 and the gas outlets 38 of the gas supply system 34. The process gas control program 140 has program code for controlling the flow rates of different constituents of the process gas. The gas flow control program 140 controls the open/close position of the safety shut-off valves, and also ramps up/down the gas flow controller 40 to obtain the desired gas flow rate. The gas pressure control program 142 comprises program code for controlling the gas pressure in the chamber 28 by regulating the aperture size of the throttle valve 44 in the exhaust system 42 of the chamber. The gas energizer control program 144 comprises program code for setting low and high-frequency RF power levels applied to the process electrodes 51, 52 in the chamber 28. Optionally, the heater control program 146 comprises program code for controlling the temperature of a heater element (not shown) used to resistively heat the support 32 and substrate 20.

The process monitoring program 126 comprises program code that obtains sample or reference signals from the plasma emission analyzer 94 or the interferometry analyzer 65 and processes the signal according to preprogrammed criteria. Typically, a radiation amplitude or spectrum trace is provided to the controller 100. The process monitoring program 126 may also send instructions to the 30 controller 100 to operate components such as the radiation source 58, radiation detector 62, the positioner 72, lens assembly 66, filter 76, and other components. The program may also send instructions to the chamber manager program 136 or other programs to change process conditions or other chamber settings.

To define the parameters of the process monitoring program 126, initially, one or more substrates 20 having predetermined thicknesses of material are selected for processing. Each substrate 20 is placed at one time into the process chamber 28 and process conditions are set to process a material 22 or an underlying material 24 on the substrate 20. Radiation reflected from the substrate 20 and/or emitted from the plasma in the chamber 28 are monitored using one or more radiation detectors 62. After a series of such traces are developed, they are examined to identify a recognizable change in a property of the trace, which is used as input for the computer program, in the form of an algorithm, a table of values, or other criteria for suitable for evaluating an event in the chamber 28 or a property of the substrate 20. For example, the process monitoring program 126 may include program code to evaluate a signal corresponding to a plasma emission or to an intensity of reflected radiation 64 which may be used to detect completion of processing of a material on the substrate 20. Thus, the computer program 126 comprises program code to evaluate first and second signals that correspond to radiation emitted from the plasma and reflected from the substrate 20. The program code evaluates an incoming signal trace provided by the analyzers 65, 94 and determines a process endpoint or completion of a process stage when a desired set of criteria is reached, such as when an attribute of the detected signal is substantially similar to a pre-programmed value. The computer program 126 may also be programmed to detect both a completion of processing of a material, for example, by detecting a change in amplitude or a rate of change of amplitude of emitted or reflected radiation. The desired criteria are programmed into process monitoring program 126 as preset or stored parameters, algorithms, or tables of values. The program 126 may also include program code for modeling a trace of radiation, selecting a feature from the modeled trace or allowing a user to select the feature, storing the modeled trace or the feature, detecting a portion of an incoming signal, evaluating the measured signal relative to the stored trace or feature, and calling an end of a process stage of the process being performed on the substrate 20 or display.

In one version, the process monitoring program 126 comprises program code for continuously analyzing a trace of a measured amplitude of radiation by drawing a box or "window" around the end portion of the trace and back in time, with signal height and time length established in the preprogrammed algorithm. A set of windows may be programmed to detect a valley or peak in the trace, trigger on an upward slope to detect a later endpoint, or to trigger on a downward slope to detect an endpoint before a valley in the trace. The first criterion is met when the signal in the trace becomes too steep and exits or moves out of the preprogrammed box ("WINDOW OUT") or when it becomes gradual and enters the box ("WINDOW IN"). Additional windows are sequentially applied on the moving trace to generate the complete set of criteria to make a determination on whether the change in signal measured in the real time trace is an endpoint of the process, a change in thickness of the material, or is only noise. The direction of entering or exiting a box may also be specified as part of the preprogrammed input criteria for operating the process monitoring program 126. Upon detecting an onset or completion of a process, the process monitoring program 126 signals the process chamber program 126 which sends instructions to the controller 100 to change a process condition in a chamber 28 in which the substrate 20 is being processed. The controller 100 is adapted to control one or more of the gas supply 34, plasma generator 46, or throttle valve 44 to change a process condition in the chamber 28 in relation to the received signal.

The present invention is described with reference to certain preferred versions thereof, however, other versions are possible. For example, the endpoint detection process can be used for detecting endpoints in other processes and in other chambers as would be apparent to one of ordinary skill, including without limitation, other types of etching chambers, such as capacitively coupled chambers; ion implantation chambers; and deposition chambers such as PVD or CVD chambers. Therefore, the spirit and scope of the appended claims should not be limited to the description of the preferred versions contained herein.

What is claimed is:

1. A substrate processing apparatus comprising:
   a process chamber capable of processing a substrate comprising a first material formed as a layer covering a plug and having a first reflectivity coefficient, and a second material about the plug that has a second reflectivity coefficient;
   a radiation source capable of emitting radiation that is reflected from the substrate during processing;
   a radiation detector to detect the reflected radiation and generate a signal trace; and
   a controller adapted to receive the signal trace and determine (i) an endpoint of processing the layer of first material and a startpoint of processing the plug of the first material from a change in the signal trace that is distinctive of an exposure of the plug of the first material and the second material having the second different reflectivity coefficient, and (ii) a depth of etching into the plug from periodic variations of the signal trace that correspond to maxima and minima interference peaks of the reflected radiation.

2. An apparatus according to claim 1 wherein the change in the signal trace corresponds to a change in intensity of the signal trace.

3. An apparatus according to claim 2 wherein the change in intensity results substantially entirely from the change in reflectivity coefficient.

4. An apparatus according to claim 1 wherein processing conditions are set to etch the first material until exposure of the second material.

5. An apparatus according to claim 1 wherein the controller comprises a computer having a memory capable of operating a computer-readable program embodied on a computer-readable medium, the computer readable program including program code to detect a change in intensity that results substantially entirely from the change in reflectivity.

6. An apparatus according to claim 1 wherein the radiation source is adapted to provide non-polarized radiation.

7. An apparatus according to claim 6 wherein the radiation source comprises a laser, LED or lamp.

8. An apparatus according to claim 1 wherein the radiation source is mounted above the substrate to direct a radiation beam at an incident angle of about 80 to 90 degrees onto the substrate.

9. A substrate processing apparatus comprising:
   (a) a chamber capable of processing a substrate comprising a first material formed as a layer covering a plug and having a first reflectivity coefficient, and a second material about the plug that has a second reflectivity coefficient;
   (b) a radiation source capable of emitting non-polarized radiation that is reflected from the substrate during processing;
   (c) a radiation detector to detect the reflected radiation and generate a signal trace; and
   (d) a computer having a memory capable of operating a computer-readable program embodied on a computer-readable medium, the computer readable program including program code to receive the signal trace and detect (i) an endpoint of processing the layer of first material and a startpoint of processing the plug of first material from a change in the signal trace that is distinctive of exposure of the plug of the first material and the second material having the second reflectivity coefficient, and (ii) a depth of etching into the plug from periodic variations of the signal trace that correspond to maxima and minima interference peaks of the reflected radiation.

10. An apparatus according to claim 9 wherein the computer readable program includes program code to determine a change in intensity of the signal trace.

11. A method of processing a substrate in a process zone, the method comprising the steps of:
   (a) placing the substrate in the process zone, the substrate comprising a first material formed as a layer covering a plug and having a first reflectivity coefficient, and a second material about the plug that has a second reflectivity coefficient;
   (b) setting process conditions in the process zone to process the first material on the substrate;
   (c) detecting radiation reflected from the substrate during processing and generating a signal trace; and
   (d) determining (i) an endpoint of processing the layer of the first material and a startpoint of processing the plug from a change in intensity of reflected radiation that is distinctive of exposure of the plug of the first material and the second material having the second different reflectivity coefficient, and (ii) a depth of etching into the plug from periodic variations of the signal trace that correspond to maxima and minima interference peaks of the reflected radiation.

12. A method according to claim 11 wherein the change in intensity results substantially entirely from the change in reflectivity coefficient from the first to the second material.

13. A method according to claim 11 further comprising directing a beam of non-polarized radiation onto the substrate.

14. A method according to claim 13 comprising directing the radiation beam at an incident angle of about 80 to 90 degrees onto the substrate.

15. A method according to claim 11 comprising setting process conditions to etch the first material to expose the second material.

16. A substrate processing apparatus comprising:
   a process chamber capable of sustaining a plasma to process a first material on the substrate;
   a first radiation detector to detect a radiation emission from the plasma and generate a first signal;
   a second radiation detector to detect a reflected radiation from the substrate and generate a second signal; and
   a controller adapted to receive the first and second signals and determine an endpoint of processing of the first material on the substrate.

17. An apparatus according to claim 16 wherein the controller is adapted to evaluate the first signal to determine an averaged state of etching of the substrate.

18. An apparatus according to claim 16 wherein the controller is adapted to evaluate the second signal to determine a change in the second signal that is distinctive of the exposure of a second material having a different reflectivity coefficient than the first material.

19. An apparatus according to claim 18 wherein the change in the second signal comprises a change in intensity that results substantially entirely from a change in reflectivity coefficient.

20. An apparatus according to claim 16 wherein the substrate comprises a second material, and wherein processing conditions are set to etch the first material until exposure of the second material.

21. A substrate processing apparatus comprising:
   a process chamber capable of sustaining a plasma to process a first material on the substrate;
   a first radiation detector to detect a radiation emission from the plasma and generate a first signal;
   a second radiation detector to detect a reflected radiation from the substrate and generate a second signal; and
   a computer having a memory capable of operating a computer-readable program embodied on a computer-readable medium, the computer readable program including program code to receive the first and second signals and determine an endpoint of processing the first material on the substrate.

22. An apparatus according to claim 21 wherein the computer readable program includes program code to evaluate the first signal to determine an averaged state of etching of the first material, and to evaluate the second signal to determine a change in signal that is distinctive of exposure of a second material having a different reflectivity coefficient than the first material.

23. A method of processing a substrate in a process zone, the method comprising the steps of:
   (a) placing the substrate in the process zone;
   (b) forming a plasma of process gas in the process zone to process a first material on the substrate;
   (c) detecting radiation emitted by the plasma;
   (d) detecting radiation reflected from the substrate; and
   (e) determining an endpoint of processing the material from a change in the radiation emitted by the plasma and a change in the radiation reflected from the substrate.

24. A method according to claim 23 comprising evaluating a change in radiation emitted by the plasma to determine an averaged state of etching of the substrate.

25. A method according to claim 23 comprising identifying a distinctive change in radiation reflected from the substrate to determine exposure of a second material having a different reflectivity coefficient than the first material.

26. A method according to claim 23 comprising identifying a distinctive change in radiation that substantially entirely results from a change in reflectivity coefficient of the substrate.

27. A method according to claim 23 comprising setting process conditions to etch the first material to expose a second material.

28. A method according to claim 23 further comprising directing nonpolarized radiation onto the substrate.

29. An apparatus according to claim 1 wherein the first material comprises polysilicon and the second material comprises an oxide or nitride material.

30. A method according to claim 11 wherein the first material comprises polysilicon and the second material comprises an oxide or nitride material.

31. An apparatus according to claim 16 wherein the second radiation detector receives radiation reflected from a region of the substrate comprising a known thickness of the first material to generate the second signal, and wherein the controller receives the second signal trace and determines an average etching rate over the substrate and a local etching rate at the region.

32. An apparatus according to claim 21 wherein the second radiation detector receives radiation reflected from a region of the substrate comprising a known thickness of the first material to generate the second signal, and wherein the controller receives the second signal trace and determines an average etching rate over the substrate and a local etching rate at the region.

33. An apparatus according to claim 1 further comprising a radiation positioner that is adapted to scan the radiation emitted by the radiation source across the substrate.

34. An apparatus according to claim 9 further comprising a radiation positioner that is adapted to scan the nonpolarized radiation emitted by the radiation source a across the substrate.

* * * * *